United States Patent [19]
Shigekawa

[11] 3,958,119
[45] May 18, 1976

[54] METHOD AND DEVICE FOR EVALUATING PENETRANTS

[75] Inventor: Toy T. Shigekawa, Orangevale, Calif.

[73] Assignee: The United States of America as represented by the Secretary of the Air Force, Washington, D.C.

[22] Filed: Aug. 5, 1974

[21] Appl. No.: 494,937

[52] U.S. Cl. ............................................. 250/302
[51] Int. Cl.² .......................................... G01N 21/16
[58] Field of Search .................. 250/302, 458, 461; 252/301.2 P, 408; 73/104; 356/237

[56] References Cited
UNITED STATES PATENTS 3,506,827   4/1970   Alburger ........................... 250/302
3,557,015   1/1971   Alburger ........................... 250/302 X

*Primary Examiner*—Davis L. Willis
*Attorney, Agent, or Firm*—Joseph E. Rusz; Cedric H. Kuhn

[57] ABSTRACT

A method is provided for evaluating fluorescent penetrants in which a penetrant to be evaluated is applied to a bevelled edge of a laminate of adhesively bonded metal sheets, the edge having shallow, parallel grooves formed therein between the metal sheets. After removal of excess penetrant from the edge, a developer is applied thereto and the edge is exposed to ultraviolet light. By observing the appearance of the bevelled edge, e.g., the brightness of the parallel lines resulting from penetrant being drawn from the grooves through action of the developer, an indication of the efficacy of the penetrant is obtained.

9 Claims, 3 Drawing Figures

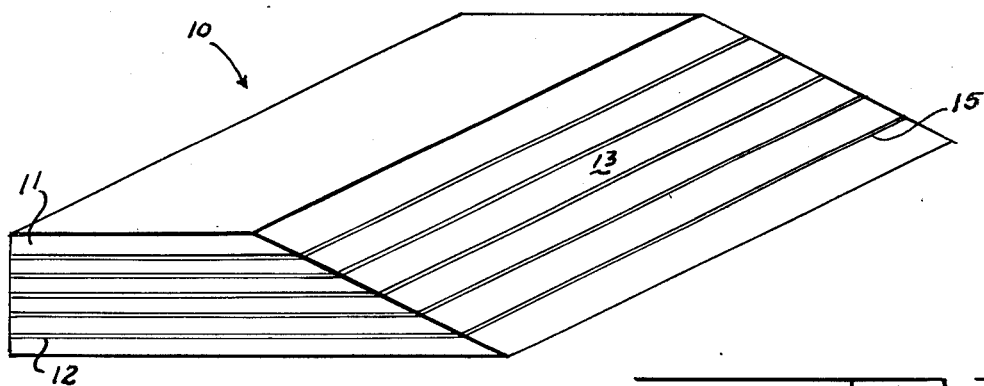
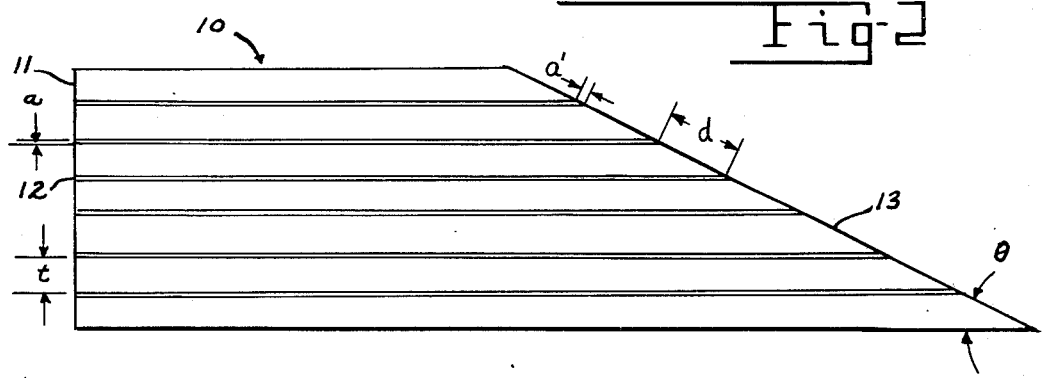
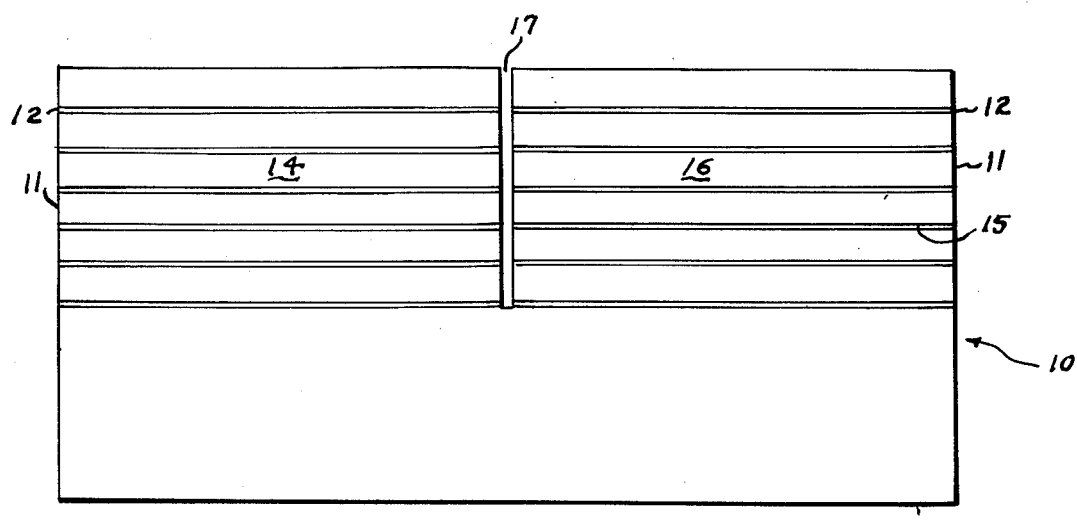

METHOD AND DEVICE FOR EVALUATING PENETRANTS

FIELD OF THE INVENTION

This invention relates to a method for evaluating the crack detecting efficiency of penetrant inspection materials. In one aspect it relates to a test device for use in evaluating visible dye and fluorescent penetrants.

BACKGROUND OF THE INVENTION

Several types of test devices have been or are employed for the purpose of evaluating the crack detecting efficiency of fluorescent penetrants. The objective of the devices is the simulation of the finer and more difficult to detect forms of flaws or cracks in metals. Included among the devices are chromium plated crack plates, brittle iron plated crack plates, quench-cracked aluminum blocks, cracked ceramic blocks, metal bars with fatigue cracks, metal sleeves bolted together under compression, and a laboratory meniscus lens apparatus for measuring the thinnest film at which a penetrant shows fluorescence upon exposure to ultraviolet light. Of these devices, the chromium plated crack plates are probably the most useful for simulating very fine cracks. However, these crack plates are not entirely satisfactory because they are quite expensive and the crack widths are not reproducible.

It is an object of this invention, therefore, to provide an improved, low cost, test device which can be mass produced to reproducible standards of "crack" widths ranging from moderately fine to coarse.

Another object of the invention is to provide a method for determining the efficacy of visible dye or fluorescent penetrants in detecting flaws or defects in objects such as aircraft structural panels, machine parts, jet engine components, and the like.

A further object of the invention is to provide a method of comparing the efficiency of two or more penetrants in detecting flaws or defects in objects.

Other objects and advantages of the invention will become apparent to those skilled in the art upon consideration of the following disclosure and the drawing in which: FIG. 1 is a perspective view of the test device of this invention;

FIG. 2 is an end view of the test device of FIG. 1; and

FIG. 3 is a plan view of another embodiment of the test device.

SUMMARY OF THE INVENTION

The present invention resides in a method for evaluating visible dye or fluorescent penetrants which comprises applying a penetrant to be evaluated to a bevelled edge or surface of a laminate of adhesively bonded metal sheets, the edge having shallow parallel grooves formed therein between the metal sheet; removing excess penetrant from the edge while leaving penetrant in the grooves; applying a developer to the edge; exposing the edge to white or ultraviolet light; and observing the appearance of the bevelled edge. The degree of brightness of parallel lines resulting from penetrant being drawn from the grooves through action of the developer gives an indication of the flaw-detecting efficiency of the penetrant.

In one embodiment of the invention, a method is provided for comparing the efficiency of two or more penetrants. Thus, at least two different penetrants are separately applied to a corresponding number of separated sections of a bevelled edge of a laminate of adhesively bonded metal sheets, the edge having shallow, parallel grooves formed therein between the sheets. After removal of excess penetrant from the edge, a developer is applied thereto and the edge is exposed to white or ultraviolet light. By observing the appearance of different sections, e.g., the brightness of the parallel lines of the sections, there is obtained a qualitative comparison of the efficiency of the different penetrants.

A better understanding of the invention can be obtained by referring to the drawing in which identical reference numerals have been used to designate similar elements. As shown in FIG. 1, test device 10 is in the form of a laminate comprising a plurality of metal sheets 11. Although it is usually preferred to employ aluminum sheets, sheets formed of other metals, such as stainless steel, mild steel or brass, can be used. The sheets are bonded to one another by means of an adhesive 12 which can be a conventional epoxy or styrene type adhesive. Commerically available laminated aluminum shim stock can be conveniently utilized in fabricating the test device. When using such shim stock, a desired thickness, e.g., ⅛ to ¼ inch, can be obtained merely by peeling off individual layers of metal.

In fabricating device 10, a laminate of any convenient size, e.g., 2 ×4 ×¼ inches, is milled along one edge to provide a bevelled surface 13. The angle between the horizontal and surface 13 can vary within broad limits, e.g, from about 10° to 30°. The actual angle selected will depend upon the desired width of parallel lines or grooves 15 and the spacing between the grooves.

The effect of the angles of machining on groove width and the spacing between grooves can be readily determined. Thus, referring to FIG. 2 of the drawing, there is shown the end view of a test device in which:

$\theta$ = the angle between bevelled edge 13 and the horizontal,
$t$ = the thickness of metal layer 11,
$a$ = the thickness of adhesive bond 12,
$a'$ = the width of groove 15, and
$d$ = the spacing between grooves 15.

From he following equations, the width of groove 15 ($a'$) and the spacing between grooves 15 ($d$) can be readily determined for any particular laminate at any chosen bevel angle:

$$a' = a/\sin\theta$$

$$d = t/\sin\theta$$

Assuming a laminate in which $t$ equals 0.002 inch and $a$ equals 0.0003 inch, when $\theta$ equals 10°, then:

$$a' = 0.0003/0.1736 = 0.00173, \text{ inch and}$$

$$d = 0.002/0.1736 = 0.0115. \text{ inch}$$

With a laminate having the same $t$ and $a$ values, when $\theta$ equals 20°, then:

$$a' = 0.0003/0.3420 = 0.000877, \text{ inch and}$$

$$d = 0.002/0.3420 = 0.00584. \text{ inch}$$

From the foregoing calculations, it is seen that for any particular laminate the larger the angle of bevel the narrower are the parallel grooves. Furthermore, the larger the angle the closer the grooves are to one another. Thus, by varying the bevel angle, the efficiency of a penetrant in detecting different size cracks can be readily determined.

After the laminate has been machined as described above, the bevelled edge is then polished and cleaned. The polishing operation can be accomplished in an manner conventionally employed for polishing metal surfaces. In one appropriate method, the edge is rubbed with emery paper, using successively finer grades. Thereafter, the smoothed edge is polished on a buffing wheel, employing a rouge buffing compound. The polished edge is then cleaned to remove any foreign matter, such as grease, dirt, buffing compound, and the like. The cleaning operation can be carried out by contacting, e.g., by wiping, the bevelled edge with an organic solvent, such as methylene chloride, trichloroethylene, and the like. Also, the device can be conveniently cleaned in a vapor degreaser.

After the polishing and cleaning operations, grooves 15 are at their narrowest and shallowest. While part of the adhesive is removed during the cleaning, it is often desirable to apply a paint stripper to the bevelled surface in order to deepen the grooves by removing adhesive. The device is then washed with water to remove the paint stripper and allowed to dry. After this treatment the grooves are very shallow so that only the brighter type of penetrants will provide a fairly visible indication of parallel lines. With the weaker penetrants, there is a much fainter indication of lines or even no indication at all.

It is usually preferred to chemically etch the bevelled surface in order to widen and deepen the parallel grooves. Thus, the grooves are cleaned out and smoothed by etching away any roughness or distortions in the edges of the metal layers. The amount of widening and deepening of the grooves will depend upon the particular etching material used and the length of time it is allowed to remain in contact with the surface. Reagents useful for etching the various metals suitable for fabricating the laminates are well known. In the case of an aluminum laminate, when a light etching action is desired, Keller's etch has been found to give good results. Keller's etch for aluminum can be formulated by mixing the following ingredients in the indicated amounts:

| Ingredient | Parts by Volume |
| --- | --- |
| Hydrofluoric acid | 2 |
| Hydrochloric acid | 3 |
| Nitric acid | 5 |
| Water | 190 |

For a stronger etching action, an aqueous solution of sodium or potassium hydroxide can be advantageously used. While the concentration is not critical, a solution containing about 20 to 30 weight percent of the hydroxide is generally employed. As a result of the etching, the grooves are enlarged and are rendered more uniform. A period of about 2 to 5 minutes is usually sufficient to obtain a desired result although longer and shorter etching times can be employed. At the end of the etching period, the device is washed with water and then dried.

Penetrant inspection materials are generally of two types, i.e., those utilizing visible dye penetrants and those using fluorescent penetrants. The penetrant materials are described in the literature and are available from several commercial sources. The penetrant inspection materials are generally sold as systems, examples of which are as follows:

1. a solvent-removable visible dye penetrant, a penetrant remover (solvent), and a dry, wet, or non-aqueous wet developer;
2. a postemulsifiable visible dye penetrant, an emulsifier, and a dry, wet, or non-aqueous wet developer;
3. a water-washable visible dye penetrant and a dry, wet, or non-aqueous wet developer;
4. a water-washable fluorescent penetrant and a dry, wet, or non-aqueous wet developer;
5. a postemulsifiable fluorescent penetrant, an emulsifier, and a dry, wet, or non-aqueous wet developer; and a high-sensitivity postemulsifiable fluorescent penetrant, an emulsifier, and a dry, wet, or non-aqueous wet developer.

In a typical test using one of the foregoing systems, a penetrant liquid is applied to the surface of a test specimen. After a soaking period of, e.g., from about 10 to 30 minutes, excess penetrant liquid is removed from the surface by an appropriate procedure which may involve use of a solvent or merely a washing with water. Depending upon the system used, an emulsifying agent may be applied to the surface prior to the washing so as to render the surface water washable. Subsequent to removal of excess penetrant, the surface of the specimen is air dried for a period of time sufficient to dry the surface but insufficient to dry penetrants in any cracks that may be present. Thereafter, the surface is coated with a developer which may be in the form of a powder. The developer functions to draw or blot residual traces of the liquid dye out of any cracks in the specimen surface. As a result of the absorption of dye by the developer, a pattern of any cracks or flaws is produced on the developer. When using visible dye penetrants, any pattern obtained should be readily visible when exposed to natural or white light. In the case of fluorescent penetrants, any patterns obtained should fluoresce when exposed to ultraviolet light.

In the inspection of metal and non-porous and plastic parts to determine material defects open to the surface, it is usually preferred to employ fluorescent penetrants. Because the test device of this invention can be produced to reproducible standards of crack widths ranging from moderately fine to coarse, it is particularly useful in evaluating fluorescent penetrants. In making such an evaluation, the fluorescent penetrant is applied to surface 13 of test device 10. After a period of about 10 to 30 minutes, excess penetrant is cleaned from the surface. Assuming that a water-washable fluorescent penetrant is used, this can be accomplished by washing the surface with water. After drying the surface, a coating of a developer, e.g., a dry powder developer, is applied thereto and the surface is exposed to ultraviolet light. An indication of the efficiency of the penetrant is obtained by observing the the brightness of the parallel lines resulting from penetrant being drawn from grooves 15 through action of the developer.

Referring to FIG. 3 of the drawing, there is illustrated a test device for comparing the efficiency of two penetrants. Initially, the device is fabricated in the same manner as described hereinabove with regard to the device of FIG. 1. However, the bevelled surface of FIG. 2 is divided into sections 14 and 16 that are separated from one another by space 17. The bevelled edge can be readily divided into two or more spaced apart sections by means of saw cuts.

The device of FIG. 3 is particularly useful for making comparative evaluations. For example, the device can be employed in making side by side comparisons between two or more lots of the same penetrant or between two or more different types of penetrants. A comparison of the brightness of the different sections provides a qualitative indication of the efficiency of the different penetrants being tested. It is to be understood that the test procedure described hereinabove would be followed except that a different penetrant would be applied to each individual section. However, it is also within the purview of the invention to use the device of FIG. 3 to compare postemulsifiable with water-washable type penetrants by applying emulsifier only to the section coated with the postemulsifiable penetrant and then washing and developing in the usual manner. Also, comparisons of the effectiveness of different developers with a given penetrant can be readily carried out. Furthermore, the device of FIG. 3 can be utilized in comparing different penetrants for their resistance to washout from the grooves under varying washing conditions.

A more complete understanding of the invention can be obtained by referring to the following illustrative examples which are not intended, however, to be unduly limitative of the invention.

EXAMPLE I

A test device of this invention was fabricated from a 2×4×¼ inch piece of laminated aluminum shim stock. The piece was ground on a belt sander along one edge, thereby producing a bevelled edge at an angle between 15° and 20° (angle $\theta$ in FIG. 2). The ground edge was smoothed with emery paper, using successively finer grades. After polishing the bevelled edge on a buffing wheel using rouge buffing compound, the polished surface was cleaned with a solvent (trichloroethylene) to remove grease, dirt, buffing compound, and any other foreign matter.

A water-washable fluorescent penetrant (P- 136 Penetrant supplied by Uresco, Inc., Downey, Calif.) was applied to the bevelled surface with its exposed grooves formed by the layers of metal. After a dwell time of 10 minutes, the test device was washed with water and dried. When the bevelled surface was examined under ultraviolet light, it was observed that the grooves had retained penetrant similar to that in a shallow crack. Application of a dry powder developer (D- 493A Developer supplied by Uresco, Inc.) intensified the fluorescent indications.

EXAMPLE II

The test device prepared as described in Example I was chemically etched after being cleaned with trichloroethylene. Thus, the polished surface was etched by contacting the surface with 10 per cent aqueous sodium hydroxide for from 2 to 3 minutes. As a result of this step, the grooves were enlarged, and there was improvement in their dimensional uniformity. When the bevelled surface was treated with the water washable penetrant and dry powder developer as described in Example I, a pattern of lines corresponding to the grooves was visible under ultraviolet light.

EXAMPLE III

A test device similar to that shown in FIG. 3 was fabricated from a piece of ¼ inch thick aluminum shim stock. One edge of the piece was milled at a 15° angle (angle $\theta$ in FIG. 2), polished with emery paper, and lightly etched with caustic solution. A saw cut was made in the bevelled edge, thereby providing two separate sections. Each section was treated with a postemulsifiable fluorescent penetrant (ZL-2 Penetrant supplied by Magnaflux Corp., Chicago, Ill.) after which the penetrant was contacted with an emulsifier (ZE-3 Emulsifier supplied by Magnaflux Corp.). The bevelled surface of each section was then washed with water, dried and dusted with a dry developer (ZP-4 Developer supplied by Magnaflux Corp.). The test device was then observed under ultraviolet light. With the exception of brighter indications due to flaws in the shim stock, the appearance of the bevelled surface of each section was the same.

EXAMPLE IV

A run was carried out in which the test device described in Example III was used to compare a postemulsifiable fluorescent penetrant (ZL-2 Penetrant supplied by Magnaflux Corp.) and a high-sensitivity postemulsifiable fluorescent penetrant (ZL-22 Penetrant supplied by Magnaflux Corp.). The bevelled surface of one section was treated with ZL-2 penetrant after which the surface was contacted with ZE-3 emulsifier. The bevelled surface of the other section was treated with ZL-22 penetrant after which the surface was contacted with ZE-3 emulsifier. The bevelled surface of each section was then washed with water, dried and dusted with ZP-4 developer. When exposed to ultraviolet light, both sections showed parallel lines corresponding to the grooves of the bevelled surfaces. However, the lines of the section to which ZL-22 was applied was brighter, indicating that ZL-22 is a more sensitive penetrant than ZL-2.

From the foregoing it is seen that the present invention provides a low cost method for determining the efficiency of penetrants in detecting defects in objects. Furthermore, the method can be advantageously employed in comparing the efficiency of two or more penetrants.

As will be evident to those skilled in the art, modifications of the invention can be made in view of the foregoing disclosure without departing from the spirit and scope of the invention.

I claim:

1. A method for evaluating the efficiency of liquid penetrants in detecting flaws which comprises applying a penetrant to be evaluated to a bevelled surface of a laminate of adhesively bonded metal sheets, the surface having shallow, parallel grooves formed therein between the metal sheets; removing excess penetrant from the surface while leaving penetrant in the grooves; applying a developer to the surface; and observing the appearance of the surface.

2. The method according to claim 1 in which the liquid penetrant is a visible dye penetrant and the appearance of the surface is observed under white light.

3. The method according to claim 1 in which the liquid penetrant is a fluorescent penetrant and the appearance of the surface is observed under ultraviolet light.

4. The method according to claim 3 in which the fluorescent penetrant is a water-washable penetrant, and excess penetrant is removed by washing the surface with water.

5. The method according to claim 3 in which the fluorescent penetrant is a postemulsifiable penetrant, and excess penetrant is removed by contacting the penetrant with an emulsifier and then washing the surface with water.

6. A method for comparing the efficiency of two or more liquid penetrants in detecting flaws which comprises separately applying at least two different penetrants to a corresponding number of separated sections of a bevelled surface of a laminate of adhesively bonded metal sheets, the surface having shallow, parallel grooves formed therein between the metal sheets; removing excess penetrant from the surface while leaving penetrant in the grooves; applying a developer to the surface, and comparing the appearance of the different sections of the surface.

7. The method according to claim 6 in which the liquid penetrants are fluorescent penetrants and the comparison of the appearance of the different sections is made by observing the surface under ultraviolet light.

8. The method according to claim 7 in which the liquid penetrants are water-washable penetrants, and excess penetrants are removed by washing the surface with water.

9. The method according to claim 7 in which the liquid penetrants are postemulsifiable penetrants, and excess penetrant is removed by contacting the penetrants with an emulsifier and then washing the surface with water.

* * * * *